United States Patent
Kafeman et al.

(10) Patent No.: US 12,007,366 B2
(45) Date of Patent: Jun. 11, 2024

(54) POWDER IDENTIFICATION SYSTEM AND METHOD

(71) Applicant: Gamlen Tableting Limited, Nottingham (GB)

(72) Inventors: Henry David Kafeman, Milton Keynes (GB); Michael Gamlen, Nottingham (GB)

(73) Assignee: Gamlen Tableting Limited, Nottingham (GB)

(*) Notice: Subject to any disclaimer, the term of this patent is extended or adjusted under 35 U.S.C. 154(b) by 596 days.

(21) Appl. No.: 17/269,675

(22) PCT Filed: Aug. 20, 2019

(86) PCT No.: PCT/GB2019/052338
§ 371 (c)(1),
(2) Date: Feb. 19, 2021

(87) PCT Pub. No.: WO2020/039182
PCT Pub. Date: Feb. 27, 2020

(65) Prior Publication Data
US 2021/0341364 A1    Nov. 4, 2021

(30) Foreign Application Priority Data
Aug. 20, 2018 (GB) ...................... 1813536

(51) Int. Cl.
*G01N 3/08* (2006.01)
*G01N 33/15* (2006.01)
*G01N 33/00* (2006.01)

(52) U.S. Cl.
CPC ............... *G01N 3/08* (2013.01); *G01N 33/15* (2013.01); *G01N 2033/0091* (2013.01); *G01N 2203/0019* (2013.01); *G01N 2203/0284* (2013.01)

(58) Field of Classification Search
CPC .. G01N 3/08; G01N 33/15; G01N 2033/0091; G01N 2203/0019;
(Continued)

(56) References Cited

U.S. PATENT DOCUMENTS 4,030,868 A    6/1977  Williams
4,099,239 A *  7/1978  Williams ............... B30B 11/005
                                                            425/149
(Continued)

FOREIGN PATENT DOCUMENTS

EP    1584454 A2    10/2005
EP    1958620 A1    8/2008
(Continued)

OTHER PUBLICATIONS

Search Report, Intellectual Property Office, United Kingdom, GB1813536.8, dated Feb. 8, 2019.
(Continued)

*Primary Examiner* — Freddie Kirkland, III
(74) *Attorney, Agent, or Firm* — Perkins IP Law Group LLC; Jefferson Perkins

(57) ABSTRACT

There is disclosed a system and method for identifying a powder material. A powder press has a die for receiving a powder to be compacted. A press member is arranged to be moveable so as to compact the powder within the die. A load sensor senses a load applied by the press member to the powder so as to generate multiple load readings during movement of the press member. A processor is arranged to receive the load readings from the load sensor and to compare the load readings during movement of the die with predetermined load data. The processor outputs an identification signal for the compacted powder based on said comparison.

18 Claims, 7 Drawing Sheets

(58) Field of Classification Search
CPC .......... G01N 2203/0284; B30B 11/005; B30B 11/02; A61J 3/10
See application file for complete search history.

(56) References Cited

U.S. PATENT DOCUMENTS

| | | | | |
|---|---|---|---|---|
| 5,838,571 | A | 11/1998 | Lewis | |
| 8,361,360 | B2* | 1/2013 | Vogeleer | B30B 11/08 |
| | | | | 264/40.5 |
| 9,950,347 | B2* | 4/2018 | Hegel | B07C 5/34 |
| 10,688,023 | B2* | 6/2020 | Gamlen | G01N 3/08 |
| 10,786,963 | B2* | 9/2020 | Gamlen | B30B 1/18 |
| 10,906,101 | B2* | 2/2021 | Weaver | B33Y 40/00 |
| 11,420,212 | B2* | 8/2022 | Gerteis | B01J 2/22 |
| 2009/0026373 | A1* | 1/2009 | Mertens | B30B 11/005 |
| | | | | 73/149 |
| 2010/0116033 | A1* | 5/2010 | Hoenderkamp | G01N 11/10 |
| | | | | 73/54.28 |
| 2014/0007784 | A1* | 1/2014 | Gamlen | G01N 3/08 |
| | | | | 100/240 |
| 2015/0374586 | A1* | 12/2015 | Gamlen | B30B 11/14 |
| | | | | 425/150 |
| 2015/0375268 | A1* | 12/2015 | Hegel | B30B 15/32 |
| | | | | 209/552 |
| 2018/0221245 | A1* | 8/2018 | Gamlen | B30B 11/025 |
| 2018/0304569 | A1* | 10/2018 | Gamlen | B30B 15/32 |
| 2019/0329266 | A1* | 10/2019 | Gerteis | B02C 23/16 |

FOREIGN PATENT DOCUMENTS

| | | |
|---|---|---|
| GB | 2544569 A | 5/2017 |
| JP | 3-71995 A | 3/1991 |
| WO | 2014001805 A1 | 1/2014 |
| WO | 2018077818 A1 | 5/2018 |

OTHER PUBLICATIONS

Written Opinion of the International Searching Authority, European Patent Office, International Patent Application No. PCT/GB2019/052338, dated Dec. 3, 2019.

International Search Report, European Patent Office, International Application No. PCT/GB2019/052338, dated Dec. 3, 2019.

* cited by examiner

```
Tab    Weight   Thick    Hard
No.    (mg)     (mm)     (kg)
1      379      4.73     1.04
2      381      4.74     1.63
3      380      4.74     1.82
LAST RESULT CANCELLED
3      378      4.71     1.43
4      380      4.72     1.86
       -----------------
       BATCH STATISTICS
       -----------------
Batch No: 3
Batch Size: 4
Min: 1.04 kg
Max: 1.86 kg
Mean: 1.49 kg
```

POWDER IDENTIFICATION SYSTEM AND METHOD

This disclosure concerns the identification of powders, and more specifically the identification of medicinal/pharmaceutical powders by assessment of the mechanical behaviour of the powder.

The large-scale production of tablets typically involves the use of tablet punches which operate to compact a volume of powder located in a die. The powder in the die is held between opposing punch parts, which move together by a predetermined distance of travel to produce a tablet of controlled thickness within a die of known geometry. This is such that the formed tablet has a known or determinable density according to the die geometry and volume of powder used but there is no direct control of the force applied to the tablet during the compaction process.

The mass production of tablets requires that the movement of the punches and/or applied load is known in advance such that a tabletting machine can be set to reproduce tablets consistently. Such machines typically allow for cyclic loading of multiple punches such that tablets can be produced continually to known production rates.

The international patent application published as WO 2012/104603 (Michael Gamlen) discloses a tablet press that offers greater control of the compaction process so as to investigate how the compaction process alters the characteristics of the tablet that is formed. The press can be used to create bespoke small batches of tablets according to user inputs for the compaction process.

There is an ongoing need to be able to verify the ingredients of medicines, such as pharmaceutical drugs. Significant effort is expended in tracking both the ingredients and the final products so that there is an audit trail throughout production and transportation. This audit trail is relied upon by the recipient to identify a received powder product.

It is desirable for many reasons to be able to positively verify the identity of a received powder, rather than having to rely entirely on an accompanying audit trail. Chemical testing and analysis techniques are conventionally used to understand the composition of a powder. However such techniques are not without drawbacks in terms of complexity and efficiency of testing. Furthermore, chemical testing may not adequately distinguish between different grades of powder material having a common chemical makeup.

It is an aim to provide an alternative method of testing medicinal/pharmaceutical powders in order to identify the powder.

STATEMENTS OF INVENTION

According to the present invention, there is provided a system for identifying a powder material, the system comprising: a press having a die for receiving a powder to be compacted, a press member arranged to be moveable so as to compact the powder within the die, and a load sensor for sensing a load applied by the press member to the powder so as to generate a plurality of load readings during movement of the press member; and, a processor arranged to receive the load readings from the load sensor and to compare said load readings during movement of the die with predetermined load data, the processor outputting an identification signal for the compacted powder based on said comparison.

The comparison may be performed based on the degree of match between one or more load reading and predetermined load data, e.g. at a common point of the compaction process or location/position of the press member relative to the die.

Additionally or alternatively, comparison may be performed based on changes in said load readings, e.g. a magnitude of change and/or rate of change in said load readings, e.g. with respect to time or movement/location of the press member.

A determination of the identification of the powder may be made by the processor by way of the comparison with the predetermined load data.

The processor may process said load readings during movement of the press member in order to generate compressibility and/or flow parameter properties/values of the powder within the die. The compressibility and/or flow parameter properties/values may be used for the comparison.

The plurality of load readings may comprise a set of load readings for a single compaction by the press, e.g. a single instance of powder compaction or a single stroke of the press member. The plurality of load readings may be taken sequentially during compaction of the powder, e.g. during a single compaction event or instance. A series or sequential load readings or continuous load readings may be taken.

Load readings may additionally or alternatively be taken during an ejection stoke by the press member, e.g. an application of load by the press member to remove/eject the powder compact form the die. Load readings may additionally or alternatively be taken during a deformation event for the powder compact using the press member, e.g. crushing/breaking the powder compact.

A plurality of sets of load readings may be taken for a common powder material to be identified, e.g. for separate compaction events/instances using the common powder material. Each compaction instance/event may be applied to a different sample of powder material, e.g. a different sample of the same powder material.

The processor may compare the plurality of sets of load readings against each other and/or against the predetermined load data. The processor may determine a degree of mismatch between the sets of load readings and compare it to a degree of mismatch between one or more of said sets and the predetermined load data.

A mathematical/statistical model may be generated to define the sets of readings collectively. A statistical distribution may be applied/fitted to the plurality of sets of readings and/or the predetermined load data.

A plot or trace of the load readings may be determined/recorded. The shape of the plot may be compared with the predetermined load data by the processor. The plot may define a compaction load trace, line, path or curve, e.g. for a single powder compaction. A set of plots may be generated for different samples of a common powder material.

The predetermined load data may comprise previously recorded load sensor data. The predetermined load data may comprise load sensor data for one or more known powder material. The predetermined load data may comprise a plurality of sets of load sensor data for a common and/or known powder material, e.g. corresponding to a plurality of different compaction events for samples of the powder material. A family or batch of sets of predetermined load data may be used, e.g. corresponding to the different compaction events for the known powder material.

The predetermined load data may comprise one or more predetermined load plot/trace, e.g. a predetermined compaction load trace, line, path or curve.

The identification signal output by the processor may comprise an indication of a match or a mismatch between the powder material and a known powder material.

According to a further aspect of the invention, there is provided a method of identifying a powder material, the method comprising: operating a press having a die for receiving a powder to be compacted by actuating a press member relative to the die so as to compact the powder within the die, sensing a load applied by the press member to the powder during compaction so as to generate load readings; and processing the load readings by comparing changes in said load readings during compaction with predetermined load data, and outputting an identification signal for the compacted powder based on a match or mismatch with predetermined load data determined by said comparison.

A plurality of samples of a common powder material may be compacted (e.g. independently) in order to generate a family of load readings, e.g. corresponding to a batch of formed powder compacts.

The family of load readings, or compaction plots, may be compared to each other to determine differences between said load readings or compaction plots. Said differences may be compared to differences between the family and the predetermined load data.

The predetermined load data may comprise a predetermined compaction plot. The predetermined load data may comprise a plurality or family of predetermined compaction plots.

The predetermined load data may comprise one or more predetermined compaction plot and envelope or threshold data for said one or more predetermined compaction plot, e.g. defining an allowable divergence from said compaction plot.

One or more portion of movement of the press member (i.e. one or more portion of the compaction process) for which the greatest difference between said load readings and said predetermined load data may be identified. The comparison may be based upon said one or more portion.

Machine learning may be used to make the comparison using any or any combination of the techniques described herein.

A mathematical analysis/model, e.g. comprising a statistical and/or pattern recognition analysis, may be used to identify differences or similarities during said comparison. A statistical distribution may be applied to load readings (or sets thereof) from different compaction events and/or the predetermined load data in order to determine one or more criterion or threshold for said comparison, e.g. for identifying a match or mismatch.

A Gaussian/normal distribution may be applied to the load readings.

A multivariate statistical distribution may be used.

The press may be operated so as to compact the powder into a solid body, such as a tablet.

An electronic controller for the press may be arranged to control the motion of the press member.

The press typically comprises one or more actuator, such as an electric motor.

The press may comprise a position and/or speed sensor for the press member.

After compaction of the powder into a solid body, deformation of the solid body of powder may be undertaken, e.g. in order to gather load readings during deformation of the solid body of powder. The load readings taken during deformation may be used for the comparison in addition to, or instead of, the load readings taken during powder compaction.

The system may comprise tablet deformation means. The tablet deformation means may comprise a tablet deformation member. The tablet deformation means may comprise an actuator for moving the deformation member and/or applying a load to a tablet. The tablet deformation means typically comprises an opposing member, such that a tablet may be located between the deformation member and the opposing member. The tablet may be compressed between the deformation member and the opposing member.

The actuator of tablet deformation means and/or the press may comprise an electrical actuator, e.g. an electromechanical actuator. An electronically controlled, electric actuator may be used. One or more electric motor may be used.

The controller of the press may allow for digital control of the press member movement, e.g. via the actuator. The controller may control actuation of the press member and/or deformation member according to a fixed/predetermined displacement value (e.g. speed) or profile. Additionally or alternatively the controller may control actuation of the press member and/or deformation member according to a fixed/predetermined load value or profile.

The press member may be arranged to compress the powder into a predetermined volume and/or to achieve a predetermined thickness of the compact.

The actuation distance of the press member and/or deformation member may be controlled and/or sensed. One or more travel/distance sensor may be provided. Sensing of the location of the press member and/or tablet deformation member may act as a calliper or compact thickness sensor. Additionally or alternatively, a separate caliper or compact thickness sensor may be provided.

A compact/tablet dimension or volume reading may be communicated to the processor.

A balance or scales for the powder and/or the formed compact may be provided. A sensed value of mass/weight may be communicated to the processor.

The tensile strength of the tablet may be determined by sensing a failure load for the formed compact under deformation.

The press and tablet deformation means may comprise the same machine or different machines arranged to output data to the processor.

The processor may output values of tabletability, compactability, flow properties and/or compressibility for each tablet. The processor may plot values of any combination of compaction pressure, solid fraction and/or tensile strength against each other. The processor may output graphs of tabletability, compactability, flow properties and/or compressibility for a common tablet material composition, which may be used during said comparison to compare with predetermined graphs of a corresponding type.

Any compressibility/flow test and/or and tablet compaction characterization procedures described herein may be performed in accordance with USP 1062—Table Compression Characterization.

According to further aspects of the invention, there is provided a method, apparatus and/or system of medicinal/pharmaceutical powder identification corresponding to the system of the first aspect or method of the second aspect.

The method may be repeated for a plurality of powder samples. Any or any combination of the steps may be automated upon operation of the press and/or receipt of the relevant data by the processor.

According to a further aspect of the invention, there is provided a data carrier comprising machine readable instructions for the operation of one or more processor to perform powder identification using the system of the first aspect or the method of the second aspect, or the data gathered by said aspect(s).

The machine readable instruction may control plotting of a plurality of values of any combination or all of compaction pressure, solid fraction and/or tensile strength on one or more graph.

According to a further aspect of the invention, there is provided a controller for a powder press to control a powder identification process in accordance with one or more of the above aspects.

Any of the optional features described herein as relating to any one aspect of the invention may be applied to any further aspect of the invention wherever practicable.

DETAILED DESCRIPTION

Various working embodiments of the invention are described below in further detail with reference to the accompanying drawings, of which:

The invention derives from the realisation that a powder press, such as a tablet press, can be used to identify or verify the identity of a powder material by assessment of the mechanical properties/behaviour of the powder under compaction. Logged sensor data can be compared to previously logged data for known powder materials to determine a match or mismatch. The surprising finding is that the mechanical/structural behaviour of a powder material under compaction can be used to positively verify the identity of the powder material in a way that is entirely independent of chemical testing.

In certain examples the compaction testing can be furthered by assessment of the manner in which powder compaction/consolidation affects one or more structural property of the formed compact/tablet, e.g. by testing of one or more mechanical/structural property of the compact/tablet.

In an overview of a system 10 for identifying powders according to the present disclosure, there is provided a powder press 12 and a data processor 14 for processing the readings taken during powder compaction in order to generate a positive or negative powder determination with reference to known powder compaction readings. The system 10 may also be used to compare different batches of powders to determine whether they are the same, regardless of whether the actual material is known.

Figure 1:
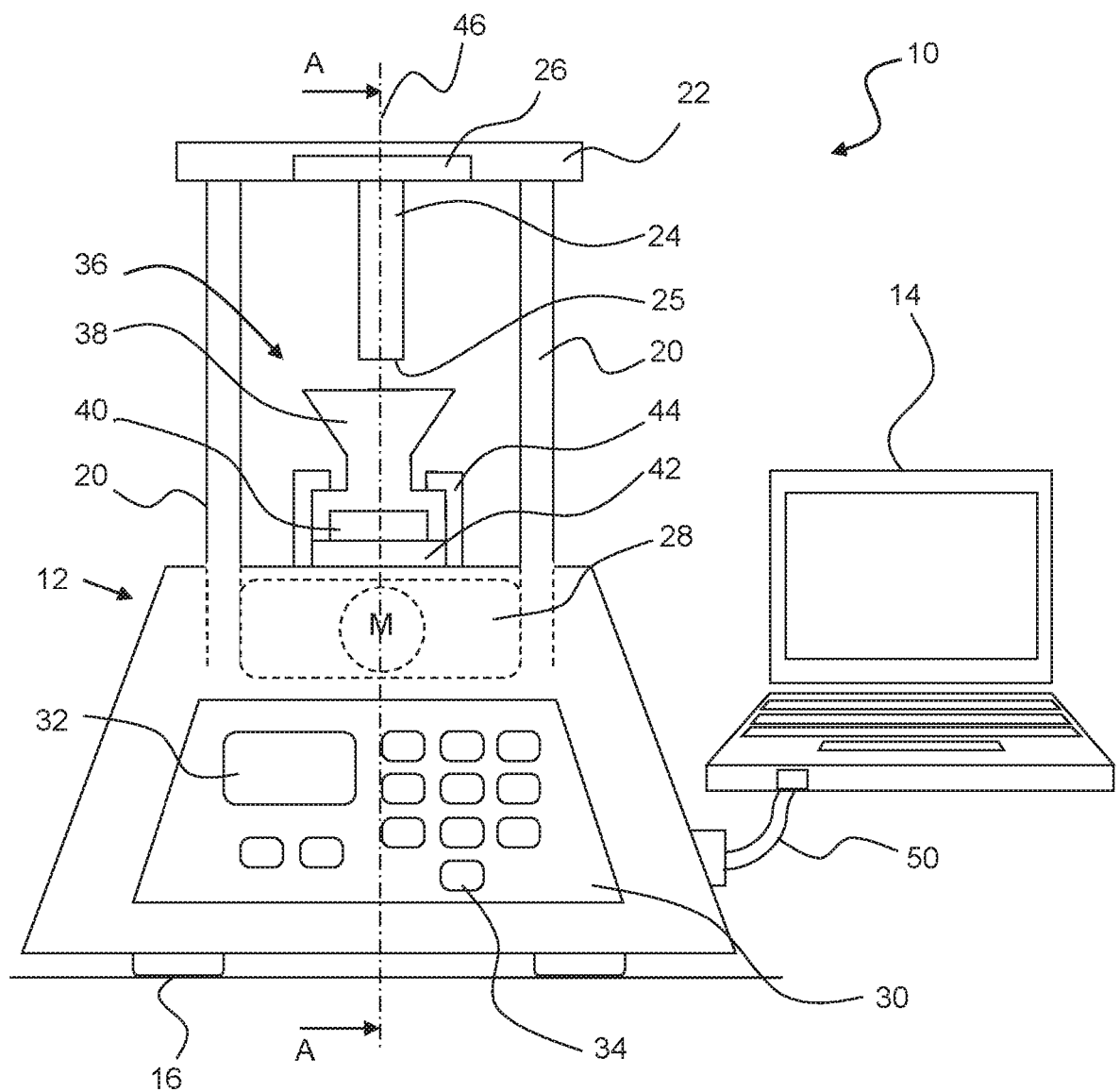
FIG. 1 shows a front view of tablet press for use in conjunction with an example of the invention.

The data processor 14 may reside within the control systems of the press 12 itself, wherein the controller of said machine may comprise one or more module of code for generation and output of a powder identification signal as described herein below. Alternatively, the data processor 14 may be comprised in separate (e.g. remote) computational/data processing equipment, as shown in FIG. 1 by way of a personal computer 14 connected to the press 12 by a wired connection 50. In other examples, the data processor 14 could be in wired or wireless data communication with the press over a network, such as a local or wide area network. The processor 14 may reside in any suitable computing equipment, such as a personal computer, laptop, mobile electronic device, server or cloud-based computational platform.

The data processor comprises one or more programmable processor, such as a computer chip, and one or more module of associated machine-readable code for processing the received compaction data. The code may control operation of a comparison process by the processor to compare the received compaction data with predetermined or previously recorded compaction data, using methods of the type described herein.

In certain examples, the data processor 14 may be in two-way communication with the press, e.g. if not provided within the press firmware, so as to be able to control operation of the press 12 and/or when data points (e.g. sensor readings) are taken using the press 12. Alternatively, the relevant control instructions for generating data points for use in powder identification may be written into the control logic/firmware of press 12 itself.

Although not shown in FIG. 1 there may typically be provided a balance for weighing and/or checking the weight of the powder prior to formation of a compact and/or the compact once formed. The mass of the compact/powder can be output from the balance and communicated to the processor 14 for use in powder assessment as discussed below. In other examples, the balance functionality may be included within the hardware of the press 10.

Whilst the following description proceeds in relation to a tablet press arranged to create a solid plug by compaction of the powder within the die, in other embodiments, it may not be necessary to compress the powder into a solid tablet-like plug. Sufficient data for powder identification could potentially be generated earlier within the compression stroke. Furthermore the process is not limited to medicinal/pharmaceutical powders but could encompass other powder materials, e.g. including metal, polymer/organic and/or ceramic powders.

In FIG. 1, there is shown an example of a tablet press 12 which may be used with the present invention. The tablet press 12 and its associated control is the focus of an earlier patent application, PCT/GB2012/050145 (GAMLEN, Michael) filed on 24 Jan. 2012 and published as WO 2012/104603 on 9 Aug. 2012, which is commonly owned by the current applicant, and in which full details of the structure, function and control of the tablet press 12 are provided. The contents of that earlier patent application are incorporated herein by reference in their entirety. The features of the tablet press 12 are not reiterated here for conciseness but it is confirmed that protection is sought herein for any features disclosed in that earlier patent application in combination with any features of the invention disclosed herein.

Figure 2:
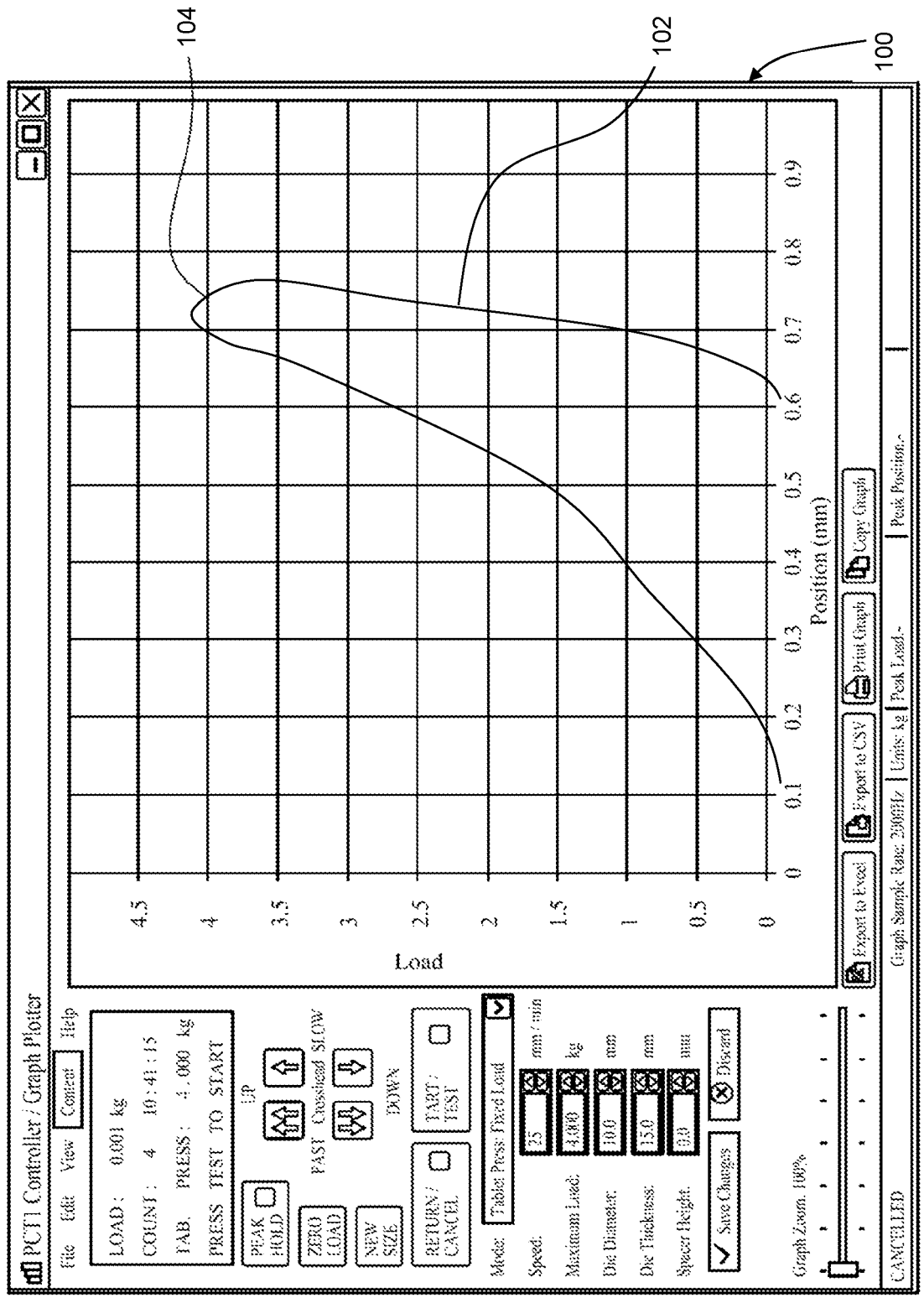
FIG. 2 shows an example of the graphical output from a tablet press of the kind shown in FIG. 1 in the form of a graphical user interface.

FIG. 2 shows a graphical interface 100 of the type described in PCT/GB2012/050145 (GAMLEN, Michael). A plot 102 of the applied load, as measured by the load cell within the tablet press 10, against the position of the press member 24 (i.e. the displacement thereof relative to the die 38 in which the powder is disposed) is provided.

The controller can thus determine the loading achieved by the press member, e.g. in units of kg or N, during compaction of the powder. This, along with any other outputs of the press controller can be communicated to the processor 14.

Since the die diameter is known and the displacement/position of the end 25 of press member 24 relative to the die floor is known, the tablet thickness, h, can be obtained and can be logged by the press controller and/or processor 14. Given the diameter/radius and thickness of the tablet, the volume, V, of the tablet (i.e. for a plain cylindrical tablet) can be determined as: $V=\pi r^2 h$.

For other tablet shapes, it will be appreciated by the skilled person that a suitable formula for the tablet volume may be substituted to the equation given above.

In other modes of operation, the tablet/compact thickness may be set by an operator as a tablet press input parameter. The press may record load applied to the powder in the die and may monitor the press member 24 position. Thus the load and position may be recorded in either mode of operation.

The compaction pressure may be determined by the tablet press controller or tablet characteriser via the equation, $P=F_c/A$, where '$F_c$' is the compaction/consolidation load applied to the powder in Newtons, and 'A' is the surface area of the formed tablet, i.e. the surface area of the press end 25, which may be calculated as $\pi r^2$ for a circular press member and tablet.

In some examples of the invention, the compaction time, or dwell time, may also be recorded. The sensing of a non-zero load may trigger recordal of load values during compaction and the return to a zero load, i.e. during retraction of the press member after the compression stroke, may cause cessation of the load recordal.

In any such examples the application of load over time may also be considered. The area under the load plot may be calculated and used as an indication of total compaction loading, akin to a measurement of total force transferred or impulse, applied to the powder when forming the tablet. This parameter may be used as an additional or alternative powder characterising parameter to the other parameters described herein.

One further benefit of using an electronically controlled, electrically-actuated tablet press of the kind described above is that the loading profile may be tailored to match that of other tablet presses if desired.

The powder compact formed in the die will typically need to be ejected. In some examples, it has been found that the ejection stroke can be used to provide additional/alternative load data for the powder material that can be used for identification of the powder (i.e. can be used as an input to the comparison with predetermined ejection load data by the comparison in order to determine a match/mismatch with the predetermined data). The ejection load data could be plotted in the same manner as in FIG. 2 if desired, e.g. as an extension of the compression plot of FIG. 2 or else as a separate plot. In some examples, the same press member can be used to compact the powder and subsequently for the ejection stroke.

Figure 3:
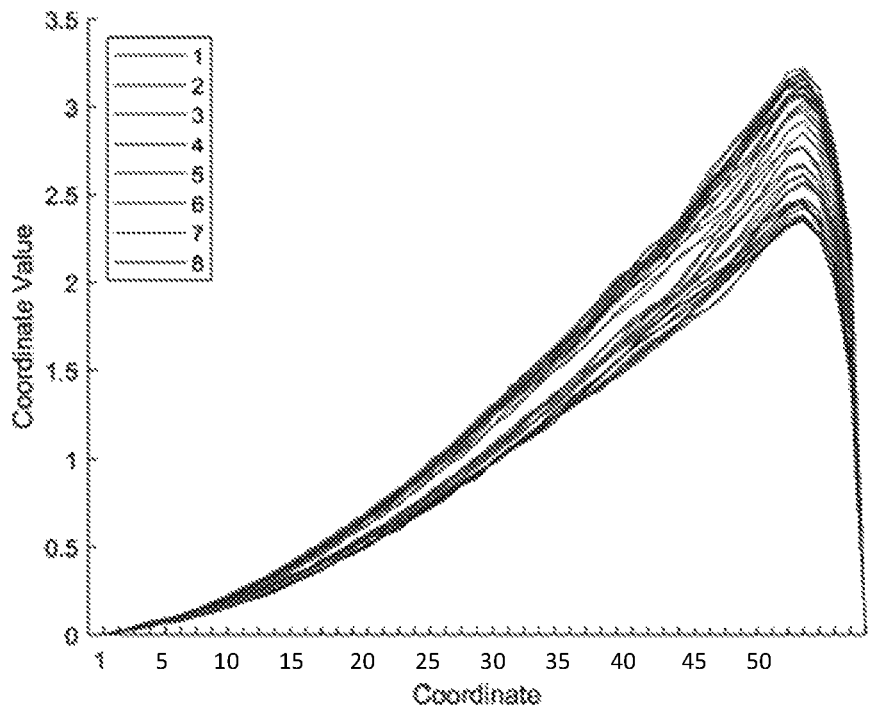
FIG. 3 shows graphs of powder loading/compaction plots for a variety of powder materials.

Turning now to FIG. 3 there is shown a series of different loading plots 102 for samples of different materials. Five different compaction events for each of the different powder materials were undertaken in this example, i.e. compacting five different samples of each material, although it will be appreciated that more samples may be used. The plots are shown as plots of load against displacement/position of the press member 24, although it would be possible also to use plots of load against time, e.g. if a common actuation speed for the press member is used.

The load may be captured as a value of applied force or pressure, or other measure that is derived therefrom.

The following description provides examples of how the shape of those plots can be interrogated and processed as part of a powder material comparison/identification process.

FIG. 3 shows that differences in peak applied load can be seen, e.g. if the press is set to compress the powder to a fixed position of the press member (i.e. corresponding to a fixed/common tablet thickness). There can be seen some splitting of the plots in the vicinity of the peak but not all materials are separated, e.g. with some plots overlapping in the vicinity of the peak. Also, in other modes of operation, it may be desirable to use a fixed peak compaction load/pressure as a press control parameter. As such, a different measure for distinguishing between the plots may be desirable.

By close inspection of the plots, it has been found that the initial phase of compaction (e.g. corresponding to the lower left portion of the graph of FIG. 3) may provide distinguishing information/separation between the different plots.

Figure 4:
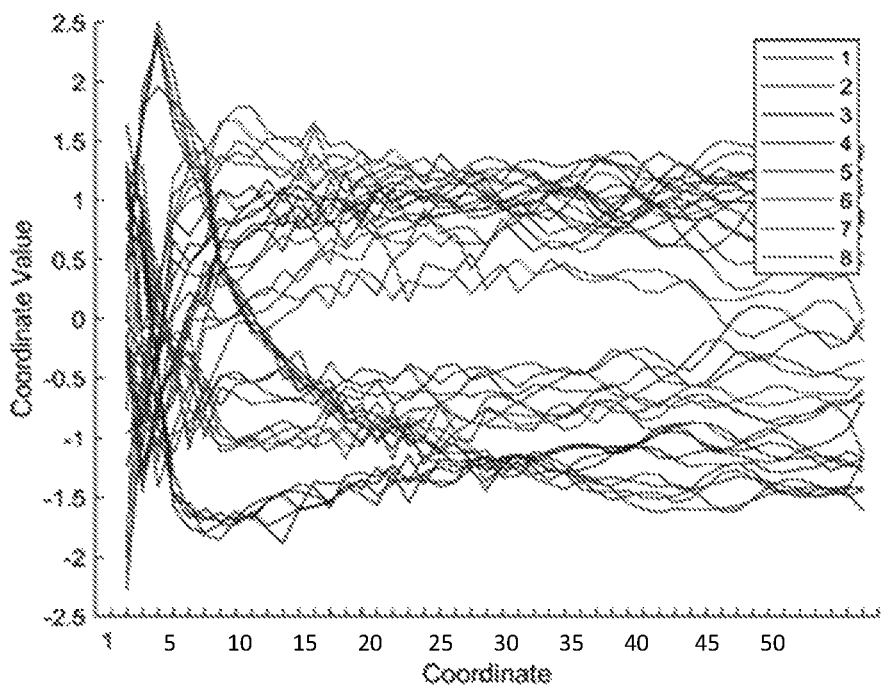
FIG. 4 shows a standardised, zoomed in graphic for the plots of FIG. 3

To compare the parts of the curves/plots on equal footing the readings at each point can be standardised and replot, as shown in FIG. 4. This shows that a majority of the variation between the plots is seen at low loads, early in the compaction process, and that past a certain level of loading, e.g. by coordinate point 10 or at least between points 10 and 20, there is relatively little change. Accordingly, aspects of the invention may concern the comparison of compressibility and/or flow parameter(s) of the powder at low pressures.

Figure 5:
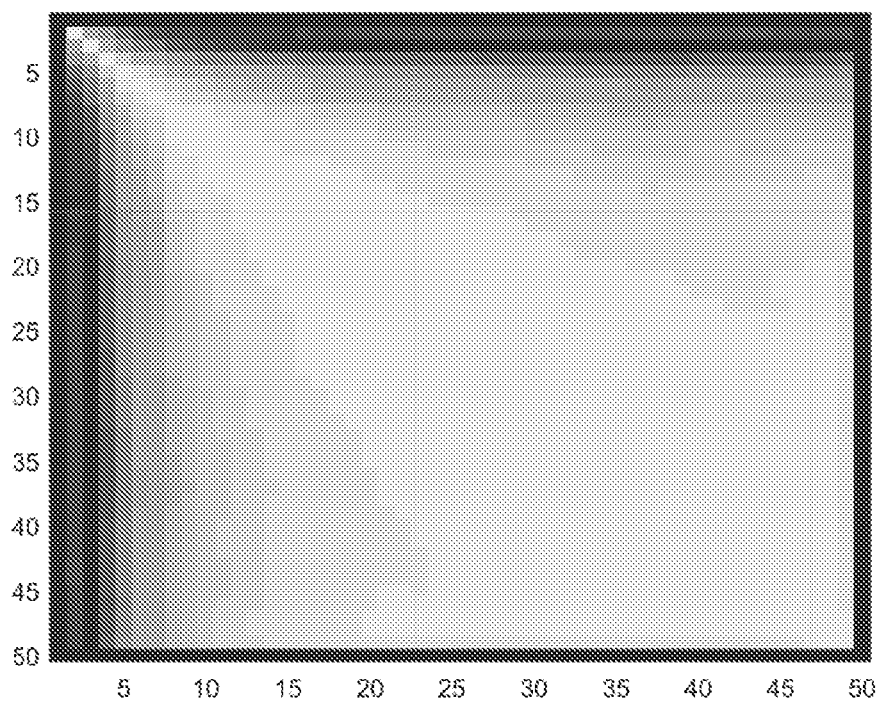
FIG. 5 shows plots of correlation matrix between different variables for the same powder materials as in FIGS. 3 and 4.
Figure 6:
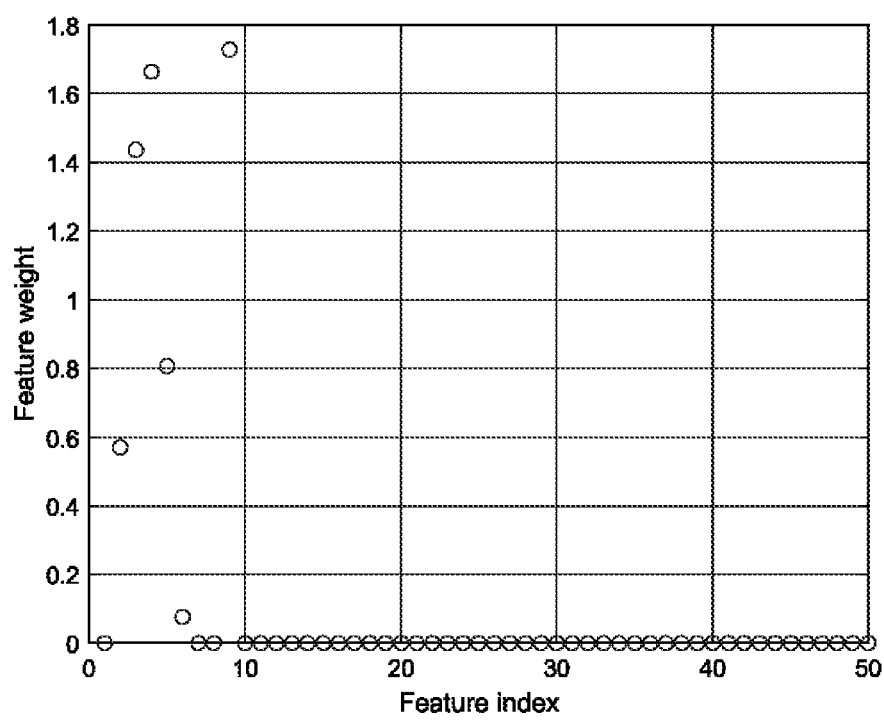
FIG. 6 shows a graph for neighbourhood coordinate analysis of the data used in FIGS. 3-5, showing the feature weight at different points.

It is important to note that this is not the only way to determine regions of interest for distinguishing between the different plots and FIGS. 5 and 6 show other examples of how the regions of greatest divergence between the plots can be identified. In FIG. 5, a correlation matrix between different variables has been plot. The darker (blue) colour regions towards the edges of FIG. 5 show greatest relative change, whereas the lighter (yellow) regions show smallest relative change. This agrees with the findings of FIG. 4 and shows that the greatest relative changes in the plots have occurred before coordinate 10 and that the later values are far more closely correlated.

In FIG. 6, a technique called Neighbourhood Coordinate Analysis is used to find the most important features in the compaction data/plots. This analysis suggests that points 2-6 and 9 contain the predominantly useful information for performing the classification/identification of the different powder materials.

In various aspects of the invention, the process may be characterised by assessment of variation between loading profiles (e.g. compressibility and/or flow characteristics) within the first half, third or quarter of the loading profile, e.g. between initiation and peak loading, cessation of the press, or the point at which loading returns to zero.

Figure 7:
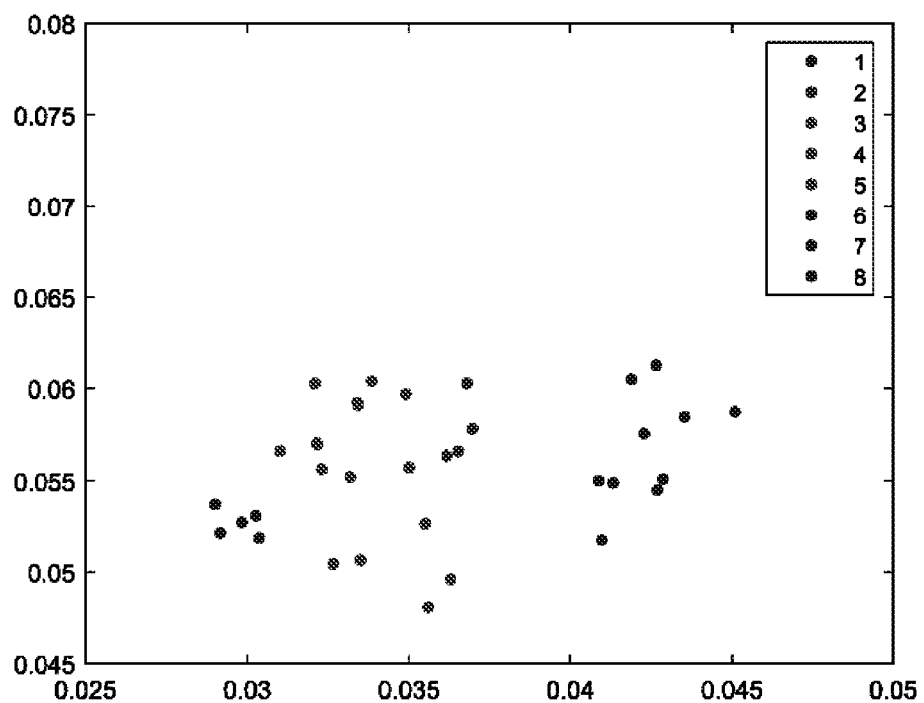
FIG. 7 shows a scatter plot for isolated portions or points of the compaction plot of FIG. 3 or 4.

Using the above information, scatter plots of the load data at corresponding points of interest for the different powder materials can be produced as shown in FIG. 7. In this example, a scatter plot of only the $3^{rd}$ and $4^{th}$ coordinate points is produced. It can be seen that the scatter plots occupy generally different regions of the available area and that the point data of different materials can be broadly separated into groups occupying a common area.

This data can be used to 'train' the process of identifying/comparing powder materials by logging the relevant data associated with one or more compaction process.

A statistical model is fitted to the available point data, e.g. akin to matching a model/distribution to available point cloud data. A linear discriminant model has been used in this example for each group of points, e.g. assuming that each group can be described by a Gaussian-type model.

It is proposed that a multivariate statistical model will be used, e.g. a multivariate Gaussian or other statistical distribution. In the example shown, a fit using only two variables is used so that it is simple to visualise, although more variables could be used if desired.

By applying a statistical distribution to the plots recorded for each powder material, average/mean values can be determined for the different groups of points (i.e. for the different materials). Furthermore maximum and minimum value thresholds for each group can be set based on desired probability levels, e.g. the amount of deviation from the mean that is permissible to allow a point to be acknowledged as belonging to the relevant group.

The thresholds may be determined using a statistical process determined to be effective based in the state of the art and the particular properties of the particular data population. Thresholds may be selected based on the likelihood of a point for the distribution lying outside of the threshold is at a desired/low level of probability (e.g. approaching zero).

Figure 8:
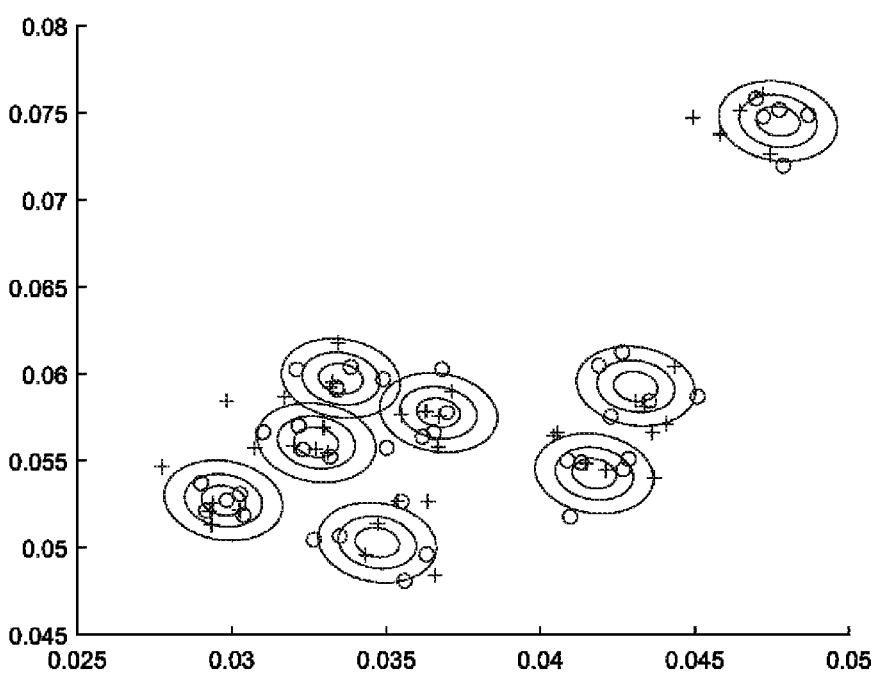
FIG. 8 shows an example of the fitment of boundaries or thresholds to the plot of FIG. 7.

In the example of a two-dimensional scatter plot of points, the averages, and max/min thresholds of each statistical model/distribution for the groups are shown as rings, e.g. as circles or ellipses in the chart of FIG. 8. Thus the bounds of the groups in two dimensional space in the chart are defined. Whilst five points are shown for simplicity in this example for each group, it is proposed that greater numbers of points will typically increase certainty and so an operator may select a suitable training batch size, i.e. the number of powder material samples used to generate a suitably accurate model of that particular powder.

Once the process has been 'trained' in this manner, and further powders that are compacted can be tested against the existing models to see if the corresponding points/data for the new powder falls within the thresholds of an existing group or not.

Whilst a single compaction test may provide sufficient information to determine whether or not the new powder falls within an existing group or not, it is considered typical that a batch of compaction tests will be performed. In this manner the batch of compaction data points can be compared to the existing statistical models to determine whether the batch as a whole matches an existing model or else defines a different material. As described above in relation to the 'training' batch size, the number of samples that are compacted as part of the comparison process may be increased/decreased to achieve a desirable level of certainty.

In the example of FIG. 8, the 'training' data/points are shown as circular nodes, whereas the new material data/points used to validate the system are shown as crosses.

When testing an unknown powder material, the similarity of points between the new batch can be compared against the existing defined group(s) to determine whether the new group is collectively contained within the existing group with a specified level of certainty, or else whether the new group is more likely to define a different group, i.e. a different statistical distribution.

Thus by using the above methodology batches of compacts can be produced to match new/unidentified powder materials with existing known powders, or else to simply verify that two materials are the same.

In practical application, this can be used by a recipient of a powder material to verify that the material is the same as another material with a relatively high degree of accuracy.

Whilst the above mathematical techniques, i.e. machine learning or AI techniques, can be used to perform the training and comparison stages, it is to be noted that other methods and models for matching the similarity/difference between these types of data plots/traces could be used.

In other examples, a support vector machine (SVM) algorithm/model can be used. A linear SVM model has been used to draw straight line boundaries between materials and to use those to define categories of new material (i.e. new data/point groups). This involved using many simple models and is more difficult to visualise. For this method also, more coordinates form the plots of FIG. 3 were used, in this example coordinates 2-6, and so this added additional dimensions to the model and respective thresholds.

However the underlying steps were the same as described above, namely that of identifying key portions of the plots at which the variance is greatest (i.e. the most promising locations for accentuating the differences between the plots) and then applying statistical modelling to multiple points or data sets representing different compaction events to identify groups.

In various different examples, it is envisaged that further statistical grouping or clustering techniques could be used.

In current developments, work is underway to assess the reproducibility of the findings between tests run on different presses, at different compaction speeds and/or on different sample volumes/masses of powder. Work is underway looking at different data normalisation techniques to one or more of those aims.

Figures 9, 10:
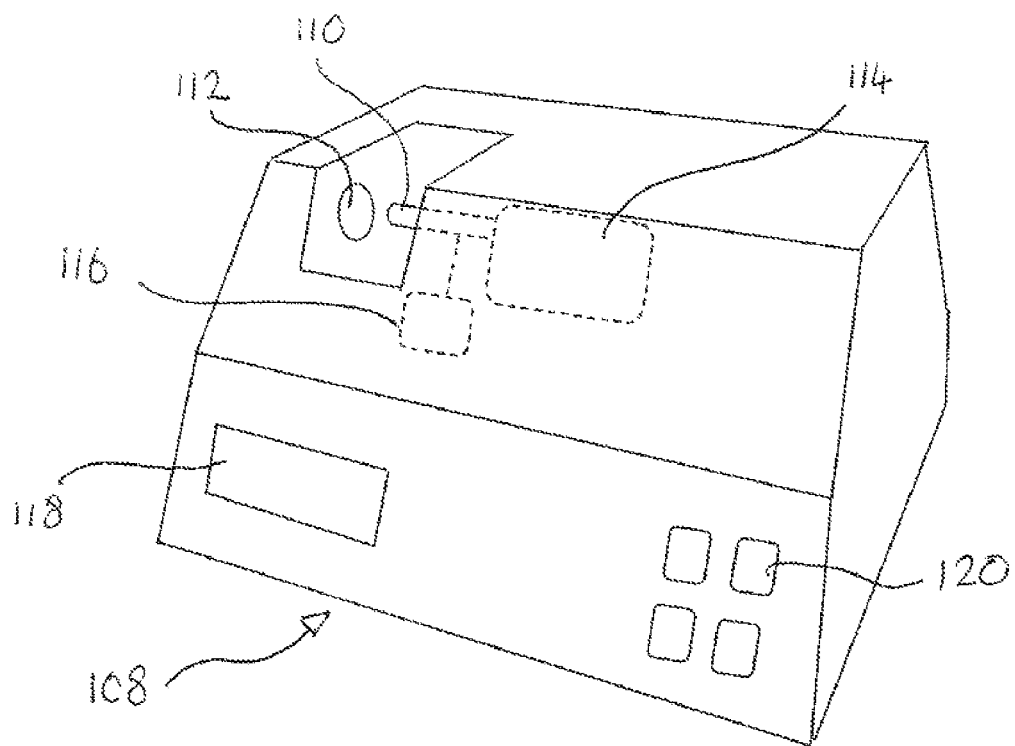
FIG. 9 shows an example of a tablet/compact compression testing device for use in conjunction with an example of the invention.
FIG. 10 shows an example output of the tablet compression testing device of FIG. 3; and, FIG. 11 shows an example of a graphical output for tablet/compact characterisation that may be used in further examples of the invention.

Turning now to FIG. 9, there is shown a tablet mechanical strength testing machine 108 for measuring tablet hardness and/or compression response.

The testing machine 108 comprises a main housing having an opening in the form of a recess into which a tablet can be inserted for compression testing. The recess comprises the tablet loading area and testing zone. The compression testing mechanism comprises a plunger 110 which is axially moveable towards a platen 112 in use. The plunger 110 can be advanced and retracted relative to the static platen 112 in a driven manner by an electric actuator 114.

The actuator 114 may comprise an electric motor DC motor under the control of an electronic controller of the kind described within PCT/GB2012/050145 (GAMLEN, Michael) for the tablet press. The motor 114 may comprise a stepper motor, such as a brushless motor, typically offering relatively high resolution angular adjustment which is converted into linear plunger actuation.

In use, a tablet is placed in-between the plunger 110 and platen 112 in the path of travel of the plunger. The plunger is advanced in a driven manner by the actuator 114 so as to contact the tablet and apply a compaction load to the tablet between the platen and the advancing plunger. The load applied to the tablet is sensed by a load sensor 116, i.e. a load cell, within the machine 108. The load sensor may be located in the force path between the actuator 114 and free end of the plunger 110—i.e. to measure the load applied via the plunger—and/or at the platen 112—i.e. to measure the reaction force of the platen when the tablet is pressed against it.

Whilst an electro-mechanical actuation system is preferred, it is feasible that other actuation mechanisms such as fluid pressure compaction systems could be used, provided they allow sufficiently fine actuation control and load increment sensing.

The speed of advancement of the plunger 110 may be adjustable. For each test, the plunger may be advanced at a substantially constant speed during compaction, for example in the region of 1-50 mm/min. A minimum advancement speed may be in the region 1-5 mm/min. The plunger may advance at a faster speed when not in contact with the tablet (i.e. when no load is sensed by the load cell and/or when the spacing between the plunger and platen is greater than a predetermined tablet dimension).

The plunger actuation control causes the plunger to continually advance at the predetermined test speed until one or more predetermined condition is achieved. In this example, the predetermined condition comprises the structural failure, or crushing, of the tablet. This is caused by the internal stress within the tablet creating a localised fracture or discontinuity in the compact to grow and thereby shear/rupture irreversibly.

The fracture detection point is measured by the controller as the point at which the maximum sensed load on the tablet drops by a pre-set percentage. The percentage load decrease is typically between 30% and 90%. A normal/default percentage load drop may be set in the region of 60%-80%, such as around 70% but this may be changed by the end user as necessary for particular tablet formulations, e.g. to account for more plastic or more brittle tablet deformation behaviour.

In a simple implementation, the controller determines and logs the applied load at, or immediately prior to tablet fracture, e.g. the maximum sensed compressive load on the tablet, in units of kg or N. In other examples, the controller may record any of the load parameters described above and in PCT/GB2012/050145 (GAMLEN, Michael) in relation to the tablet press. That is to say, the controller may record a continuous or multiple readings for applied pressure/load up to yield/fracture of the tablet.

In some examples, the actuation of the plunger may be used to determine one or more tablet dimension, for example by advancing the plunger 110 up to the point at which the tablet against the platen 112 resists further advancement. A tablet diameter or thickness may be measured in this manner. Alternatively, a caliper may be attached to the machine 12, e.g. for communication with the machine controller such that one or more tablet dimension can be measured and recorded.

The tablet dimension may be sensed as an automatic sizing routine by the machine 108. The tablet dimension (e.g. thickness) may be logged for each tablet in a batch such that statistical analysis of the batch tablet dimensions can be performed.

In the event that a balance is not used in conjunction with the tablet press 10, one may be used in conjunction with the testing machine 108, for example by connecting the balance to the machine 108 for communication of tablet mass/weight with the machine controller prior to compaction testing. Batch statistical analysis can be performed on the tablet weights as necessary.

Storage, recall and statistical analysis of the recorded fracture loads may be performed by the controller. The fracture load provides an indication of tablet hardness. Maximum, minimum, mean and/or standard deviation values for a batch of tablets can be produced.

The outputs from the machine 108 can be communicated to the processor 14, which may be common to both the press 10 and machine 108. An example of batch results logged by the machine 108 is shown in FIG. 10.

The breaking force (i.e. the fracture force) output by the machine 12 controller can be converted to a tensile strength, σ, value for the tablet using:

$$\sigma = 2F_B/\pi dh$$

where $F_B$ is the tablet break force under diametral compression, d is the tablet diameter and h is the tablet thickness. The tablet dimension values may be determined using any of the techniques described above. The skilled person will appreciate that the above equation may vary for tablets that differ from a cylindrical tablet form.

The processor 14 can determine the solid fraction (SF) for each tablet using the equation:

$$SF = Wt/\rho \cdot v$$

where Wt is the tablet weight, ρ is the true density of the powder material used in the tablet formation and v is the tablet volume determined by one of the machine controllers described above or the processor 14. The true density of the tablet material, i.e. the density of the formulation, including excipient, may be input by the user based on the available material properties.

The tablet porosity, ε, may be determined if necessary by the tablet characteriser as $$\varepsilon = 1 - SF.$$

Figure 11:
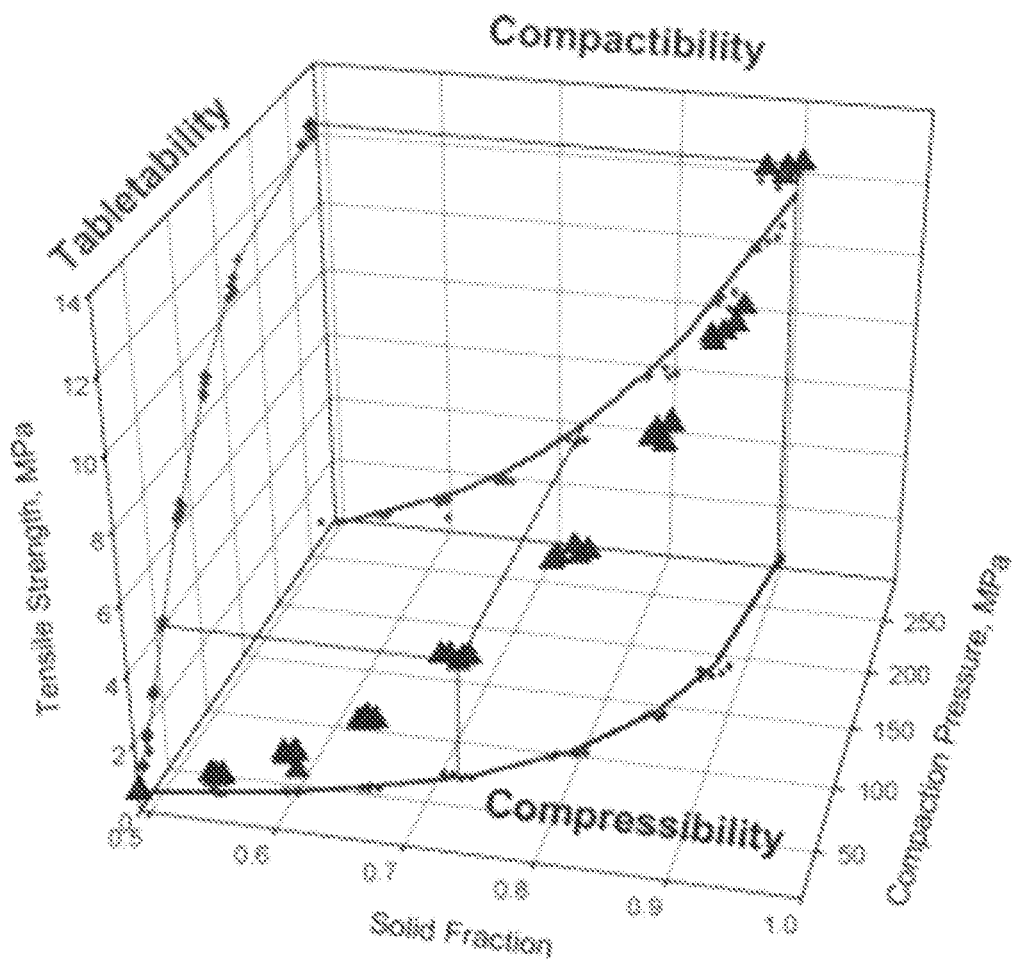

Turning now to FIG. 11 three graphs may be constructed for a particular tablet composition/formulation as follows:
Tabletability: tensile strength (MPa) against compaction pressure (MPa)
Compactability: tensile strength (MPa) against solid fraction (non-dimensional)
Compressibility: solid fraction against compaction pressure (MPa)

The graphs may be plotted in the manner as shown in FIG. 11 so as to define any or any combination of three orthogonal axes for each of tensile strength, compaction pressure and solid fraction. Thus each measured tablet may represent a point in three-dimensional space, wherein each of the three orthogonal coordinate values represents a point in two-dimensional space on each of the 2D graphs described above. That is to say each tablet may be characterised by its three values of tensile strength, compaction pressure and solid fraction.

One benefit of such a system is that, for a batch of tablets formed using the same tablet composition but using different compaction parameters, i.e. a different compaction pressure, the resulting solid fraction and tensile strength values will cause a plot in three dimensional space shown as the triangular point data in FIG. 11. The corresponding tabletability, compressibility and compactability plots in the two-dimensional space containing the axes shown in FIG. 11 can be determined by the tablet characteriser from, or instead of, the three-dimensional plot.

In this manner structural properties can be investigated and interrogated simply and consistently using a standardised system and procedure. This allows other sources of mechanical/structural compact behaviour for compacts produced using the press 10 to contribute to tablet identification. It may also allow further investigation into other related considerations, such as crystal structure, polymorphism, granulation, solvent use in wet granulation and the like, since the invention provides a useful framework and associated equipment, through which powder material selection can cause isolated changes in tablet structure and associated properties.

It has also been found that the apparatus described herein can be used to generate one or more flow parameter property for the powder. One or more flow parameter may be used for the comparison with existing data to identify the powder, e.g. in addition to or instead of the compressibility or compaction property of the powder.

Thus any or any combination of the measurements taken, or the calculations derived therefrom for tablet structural properties may be processed in the same way as the compaction data recorded during tablet compaction (i.e. powder flow) to allow comparison between powders to determine a match or mismatch there-between. It is proposed that these additional measurements can be used to further improve accuracy in combination with the data recorded during compaction. However in other examples, it is possible that such data could be used to identify/classify the powder content of a pre-compacted solid in isolation of the compaction process.

Whilst the above examples show the press 10 and compact testing machine 108 as two separate machines in communication with a common processor 14, it will be appreciated that certain data may be shared between said machines. In yet further examples of the invention a common machine may be devised which is capable of implementing both the press and compaction/fracture testing functionality, e.g. using a common actuation and/or sensing system. In some examples, the press member may be used as a fracture testing plunger or vice versa. The powder die may be removable and/or replaceable with a platen for testing of the tablet once formed.

Furthermore, whilst the above examples focus mainly on powders for tablet production and pharmaceutical use, the invention is not limited thereto. It has been found that the invention has many potential applications. One example involves the use of powders for 3D printing. The 3D printing process can be wasteful, e.g. whereby only a fraction of the powder loaded into the 3D printer resides in the final printed body. As such the reuse of wasted powder offers significant improvements in efficiency. However it is unclear the extent to which powder can be reused and what volume of virgin/fresh powder is required. The invention may allow testing/identification of powder makeup for such applications as a further example of use.

The invention claimed is:

1. A system for identifying a powder material, the system comprising:
a press having a die for receiving a powder to be compacted, a press member arranged to be moveable so as to compact the powder within the die, and a load sensor for sensing a load applied by the press member to the powder so as to generate a plurality of load readings during movement of the press member; and,
a processor arranged to receive the load readings from the load sensor and to compare said load readings during movement of the die with predetermined load data, the processor outputting an identification signal for the compacted powder based on a match or mismatch with predetermined load data determined by said comparison,
wherein the identification signal comprises an indication of a match or mismatch between the powder material and a known powder material.

2. A system according to claim 1, wherein the comparison is performed based on the degree of match between one or more load reading and the predetermined load data at one or more common point of the compaction process.

3. A system according to claim 1, wherein the plurality of load readings comprise a set of load readings for a single instance of powder compaction by the press.

4. A system according to claim 1 wherein a plurality of sets of load readings are taken using different samples of a common powder material to be identified, and the processor compares the plurality of sets of load readings against each other and/or against the predetermined load data.

5. A system according to claim 4, wherein the processor determines a degree of mismatch between the sets of load readings and compares it to a degree of mismatch between the sets of load readings and the predetermined load data.

6. A system according to claim 1, wherein the processor applies a statistical model to the sets of load readings.

7. A system according to claim 1, wherein the predetermined load data comprises a statistical distribution and the processor determines whether one or more of the plurality of load readings is a fit with the statistical distribution.

8. A system according to claim 1, wherein the plurality of load readings and/or predetermined load data comprise a plot of load readings during a compaction event and/or ejection event for the powder compact and wherein the processor compares a shape attribute of the plot with the predetermined load data.

9. A system according to claim 1, wherein the predetermined load data comprises previously recorded load sensor data comprising a plurality of sets of load sensor data corresponding to a plurality of different compaction events for samples of the powder material.

10. A system according to claim 1, wherein the identification signal output by the processor comprises an indication of a match or a mismatch between the powder material and the predetermined load data.

11. A system according to claim 1, wherein the processor is arranged to determine a powder compressibility and/or flow parameter value from the load data and to perform the comparison with the predetermined data based thereon.

12. A method of identifying a powder material, the method comprising:
operating a press having a die for receiving a powder to be compacted by a press member and actuating the press member relative to the die so as to compact the powder within the die
sensing a load applied by the press member to the powder during compaction so as to generate load readings;
processing the load readings by comparing load readings during compaction with predetermined load data; and
outputting an identification signal for the compacted powder based on a match or mismatch with predetermined load data determined by said comparison,
wherein the identification signal comprises an indication of a match or mismatch between the powder material and a known powder material.

13. A method according to claim 12, wherein the predetermined load data comprises a predetermined compaction load plot and threshold data for one or more points in said predetermined compaction plot, said threshold data defining an allowable divergence from said compaction plot.

14. A method according to claim 12, comprising determining one or more portion of the compaction process for which a greatest difference between said load readings and said predetermined load data can be identified, and performing the comparison based upon said one or more portion.

15. A method according to claim 12, comprising performing the comparison between load readings taken during the first half or third of the compaction of the powder.

16. A method according to claim 12 comprising repeating the operation of the press for different samples of the same powder material to generate different sets of load readings and fitting a statistical distribution to the sets of load readings.

17. A method according to claim 12, wherein the predetermined load data comprises a multivariate statistical distribution for previously obtained powder compaction load readings.

18. A method according to claim 12, comprising using machine learning to generate the predetermined load data and/or perform the comparison based on a plurality of powder compaction events using different samples of a common powder material.

\* \* \* \* \*